US006565768B1

(12) United States Patent
Dentler et al.

(10) Patent No.: US 6,565,768 B1
(45) Date of Patent: *May 20, 2003

(54) METHOD FOR PRODUCING WATER-SWELLABLE HYDORPHILIC POLYMERS, SAID POLYMERS AND USE THEREOF

(75) Inventors: Joachim Dentler, Bruchköbel (DE); Norbert Herfert, Altenstadt (DE); Rudolf Schliwa, Alzenau (DE); Uwe Stüven, Bad Soden (DE); Fritz Engelhardt, Chesapeake, VA (US)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/806,942
(22) PCT Filed: Sep. 28, 1999
(86) PCT No.: PCT/EP99/07176
§ 371 (c)(1),
(2), (4) Date: Apr. 6, 2001
(87) PCT Pub. No.: WO00/22017
PCT Pub. Date: Apr. 20, 2000

(30) Foreign Application Priority Data

Oct. 8, 1998 (DE) .......................... 198 46 413

(51) Int. Cl.⁷ .............................. C09K 3/00
(52) U.S. Cl. ................. 252/194; 264/177.17; 516/108; 523/312; 524/801; 524/832; 524/833; 524/916; 526/932; 528/930
(58) Field of Search .......................... 516/108; 524/832, 524/833, 916, 801; 264/177.17; 252/194; 523/312; 528/930; 526/932

(56) References Cited

U.S. PATENT DOCUMENTS

| 4,076,663 A | | 2/1978 | Masuda et al. | |
|---|---|---|---|---|
| 4,113,688 A | * | 9/1978 | Pearson | 524/916 X |
| 4,798,861 A | * | 1/1989 | Johnson et al. | 524/801 X |
| 4,873,299 A | | 10/1989 | Nowakowsky et al. | 526/73 |
| 4,985,514 A | | 1/1991 | Kimura et al. | 526/88 |
| 5,250,640 A | | 10/1993 | Irie et al. | 526/88 |
| 5,275,773 A | * | 1/1994 | Irie et al. | 524/916 X |
| 5,453,323 A | | 9/1995 | Chambers et al. | 428/402 |
| 5,629,377 A | * | 5/1997 | Burgert et al. | 524/832 |
| 5,668,236 A | * | 9/1997 | Engelhardt et al. | 524/916 X |

FOREIGN PATENT DOCUMENTS

| DE | 26 12 846 | 1/1981 |
|---|---|---|
| DE | 195 29 348 | 2/1997 |
| EP | 0 205 674 | 12/1986 |
| EP | 0 238 050 | 9/1987 |
| EP | 0 303 440 | 2/1989 |
| EP | 0 530 438 | 3/1993 |
| EP | 0 629 411 | 12/1994 |
| WO | WO 97/06190 | 2/1997 |

* cited by examiner

*Primary Examiner*—Richard D. Lovering
(74) *Attorney, Agent, or Firm*—Oblon, Spivak, McClelland, Maier & Neustadt, P.C.

(57) ABSTRACT

Water-swellable hydrophilic polymers are prepared by neutralization of the acidic hydrogel having a degree of neutralization of 0–40 mol % to an ultimate degree of neutralization of 60–85 mol % by mixing with a neutralizing agent in a mincer comprising a system of screw, rotating blade, restricted flow zone and breaker plate, wherein the mincer has a power output of from 1000 to 6000 Wh/m³ the hydrogel passes through a zone having an energy dissipation density of from 400 to 800 W/l of mixing volume the average residence time of the hydrogel in the mincer is from 5 to 30 seconds the breaker plate has an open area of from 20 to 40%.

26 Claims, No Drawings

METHOD FOR PRODUCING WATER-SWELLABLE HYDORPHILIC POLYMERS, SAID POLYMERS AND USE THEREOF

This application is a 371 of PCT/EP 99/07176, filed Sep. 28, 1999.

The present invention relates to a process for preparing water-swellable hydrophilic polymers, to the polymers obtained thereby and to the use of these polymers.

Hydrophilic hydrogels are obtainable by polymerization of unsaturated acids, for example acrylic acid, methacrylic acid, acrylamidopropanesulfonic acid, etc., in the presence of small amounts of multiply olefinically unsaturated compounds are already known as superabsorbent polymers.

Also known are hydrophilic hydrogels obtainable by graft copolymerization of the olefinically unsaturated acids onto different matrices, for example polysaccharides, polyalkylene oxides and derivatives thereof.

The hydrogels mentioned are notable for high absorbency for water and aqueous solutions and are therefore widely used as absorbants in hygiene articles.

Such water-swellable hydrophilic polymers are generally prepared by free-radical polymerization in an aqueous solution which contains the monomers with or without a grafting base and crosslinker.

The water-swellable hydrophilic polymers produced for use in the hygiene and sanitary sector have a degree of neutralization in the range from 60 to 85 mol % based on the polymerized acid-functional monomer units, so that the hydrogels formed in use are pH neutral with regard to the skin.

The degree of neutralization is generally set prior to the polymerization, since this avoids the technically difficult neutralization of an acidic hydrogel of high viscosity. However, the polymerization of, for example, acrylic acid in the neutral pH range is slower, and leads to lower molecular weights, than the polymerization in the acidic range. This is explained by the electrostatic repellency between the most recently incorporated monomer unit and the next monomer unit to be incorporated, which repellency arises only minimally, if at all, in the case of a polymerization in the acidic pH range, since the monomer units are present in the uncharged, acidic form.

The trend toward ever thinner diaper constructions requires water-swellable hydrophilic polymers providing better and better performance characteristics with regard to absorption capacity, gel strength, gel permeability and residual extractables.

The desired combination of high absorption, high gel strength, high gel permeability and low residual extractables can only be provided by a polymerization where very high molecular weights are obtained for the primary polymer chains. The preferred way to provide such products is therefore a polymerization in aqueous solution where the acid-functional monomer units present in the monomer solution are only partly preneutralized, if at all. The degree of neutralization of the acid-functional monomers is preferably in the range from 0 to 40 mol %, particularly preferably in the range from 0 to 25 mol %.

Polymerization and subsequent coarse comminution provides acidic hydrogel particles which have to be adjusted to the desired ultimate degree of neutralization of 60–85 mol % based on acid-functional monomer units by neutralizing these acid-functional monomer units. This neutralization is a process which is technically difficult to carry out and which has to meet particular requirements. First, the gel must not be excessively sheared during the contacting with the neutralizing agent so as to avoid increasing the extractables content, which would have an adverse effect on the properties of the end product and accordingly is undesirable. Secondly, neutralization has to be completely homogeneous in order that sufficiently good drying characteristics may be obtained for the gel particles. This is because acidic hydrogel particles having a low degree of neutralization are very tacky and are incapable in the subsequent belt drying of forming the loose assembly that is needed if high drying rates are to be obtained.

The subsequent neutralization of acidic hydrogels is known in principle.

DE-A-26 12 846 discloses a process for preparing a water-absorbing resin by polymerizing at least one starch and/or cellulose with at least one water-soluble monomer having a polymerizable double bond and with a crosslinker. The polymers obtained are neutralized with bases, although the method of neutralization is not more particularly specified.

According to EP-A-0 205 674, acidic polymers are prepared at from 0 to 100° C., preferably from 5 to 40° C., and their pH is adjusted by subsequent partial neutralization of the hydrogel. Neutralization is effected here by adding the gel to a very dilute sodium hydroxide solution. This method is disadvantageous, since large amounts of water have to be evaporated at the drying stage owing to the very dilute nature of the sodium hydroxide solution.

EP-A-0 303 440 describes the production of a hydrated crosslinked gel polymer which has 10 to 50 mol % of the acid-functional monomers neutralized and which is adjusted to the desired ultimate degree of neutralization by adding a neutralizing agent in a reaction vessel having a plurality of rotary shafts each fitted with stirring blades. True, this process provides homogeneous neutralization, since new surfaces are constantly being generated for the gel particles, but the shearing force on the gel is too high and leads to an undesirable increase in extractables.

EP-A-0 238 050 claims a process for the batchwise production of finely divided crosslinked water-absorbing polymers by conducting the polymerization in a kneader and having a degree of neutralization for the (meth)acrylic acid in the range from 0 to 100 mol %. The polymerization batch is neutralized to the desired ultimate pH in the kneader used for the polymerization, either during the polymerization or subsequently thereto. This again provides homogeneous neutralization, but the shearing forces applied are too high, so that an undesirable increase in the extractables content occurs.

In U.S. Pat. No. 5 453 323 and EP-A-0 530 438, acrylic acid is used together with water-soluble hydroxyl-containing polymers to prepare under adiabatic conditions and without neutralization of the monomers polymer gels which are subsequently comminuted in an unspecified meat grinder. The neutralizing agent is added to this comminuted gel and the mixture is again chopped. The postcrosslinker is then added and the gel is again chopped three times in order that all the reactants may be incorporated in the gel in a homogeneous manner. This repeated chopping of the gel exerts an undesirable shearing stress on the gel, elevating the level of extractables.

EP-A-0 629 411 describes the polymerization of acrylic acid with crosslinkers. The gel obtained is subsequently partially neutralized with an alkali metal salt and further crosslinked by addition of a crosslinker. The method of neutralization is not further specified in the reference; one example mentions kneading the gel with the neutralizing agent in an extruder.

DE-A-195 29 348 describes preparing superabsorbent polymers by polymerizing a partially preneutralized monomer solution under adiabatic conditions. The degree of preneutralization of the acid-functional monomers is in the range from 5 to 30 mol %. The acidic gel is neutralized after its comminution in simple mixing assemblies such as a rotating drum or in a Drais mixer, the aqueous solution of the bases being introduced via nozzles or spray injectors, for example. True, this avoids any mechanical damage to the polymer gel, but cannot provide homogeneous neutralization, since the gel is not destructured in the course of the mixing with the neutralizing agent. The pH inhomogeneities of the gel in turn lead to inferior drying, which is undesirable for economic reasons.

It is an object of the present invention to provide a process for postneutralizing acidic hydrogels homogeneously and with minimal shear stress on the gel to avoid an undesirable increase in the extractable fractions.

We have found that this object is achieved by the process for preparing water-swellable hydrophilic polymers by neutralization of the acidic hydrogel having a degree of neutralization of 0–40 mol % to an ultimate degree of neutralization of 60–85 mol % by mixing with a neutralizing agent in a mincer comprising a system of screw, rotating blade, restricted flow zone and breaker plate, wherein the mincer has a power output of from 1000 to 6000 Wh/m³ the hydrogel passes through a zone having an energy dissipation density of from 400 to 800 W/l of mixing volume the average residence time of the hydrogel in the mincer is from 5 to 30 seconds the breaker plate has an open area of from 20 to 40%.

Preference is given to a process for preparing water-swellable hydrophilic polymers, which comprises
a) free-radically (co)polymerizing one or more hydrophilic monomers or graft (co)polymerizing one or more hydrophilic monomers onto a grafting base, the average degree of neutralization of the acid-functional monomers being from 0 to 40 mol %;
b) coarsely comminuting the acidic hydrogel;
c) neutralization of the acidic hydrogel to an ultimate degree of neutralization of 60–85 mol % by mixing with a neutralizing agent in a mincer comprising a system of screw, rotating blade, restricted flow zone and breaker plate, wherein
the mincer has a power output of from 1000 to 6000 Wh/m³
the hydrogel passes through a zone having an energy dissipation density of from 400 to 800 W/l of mixing volume
the average residence time of the hydrogel in the mincer is from 5 to 30 seconds
the breaker plate has an open area of from 20 to 40%;
d) placing the neutralized hydrogel particles without further mechanical shearing stress onto a belt dryer;
e) drying the hydrogel particles using a belt dryer and
f) grinding and sieving the dried hydrogel particles.

The process of the invention will now be more particularly described.

Hydrophilic monomers useful for preparing the water-swellable hydrophilic polymers of the invention include for example acids capabale of addition polymerization, such as acrylic acid, methacrylic acid, vinylsulfonic acid, vinylphosphonic acid, maleic acid, maleic anhydride, fumaric acid, itaconic acid, 2-acrylamido-2-methylpropanesulfonic acid, 2-acrylamido-2-methylpropanephosphonic acid and their amides, hydroxyalkyl esters and amino- or ammonio-functional esters and amides. Water-soluble N-vinylamides or else diallyldimethylammonium chloride are also suitable.

Preferred hydrophilic monomers are compounds of the general formula (I)

where
$R^1$ is hydrogen, methyl or ethyl,
$R^2$ is —COOR⁴, hydroxysulfonyl, phosphonyl, a $(C_1$–$C_4)$-alkanol-esterified phosphonyl group or a group of the formula (II)

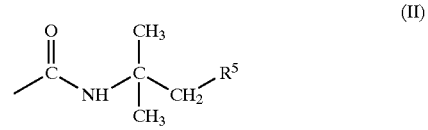

where
$R^3$ is hydrogen, methyl, ethyl or carboxyl,
$R^4$ is hydrogen, amino-$(C_1$–$C_4)$-alkyl or hydroxy-$(C_1$–$C_4)$-alkyl, and
$R^5$ is hydroxysulfonyl, phosphonyl or carboxyl.

Examples of $(C_1$–$C_4)$-alkanols are methanol, ethanol, n-propanol and n-butanol.

Particularly preferred hydrophilic monomers are acrylic acid and methacrylic acid.

When the monomers used are acids, their alkali metal or ammonium salts may be used as comonomers in a fraction of up to 40% by weight.

Useful grafting bases may be of natural or synthetic origin. Examples are starch, cellulose or cellulose derivatives and also other polysaccharides and oligosaccharides, polyvinyl alcohol, polyalkylene oxides, especially polyethylene oxides and polypropylene oxides, and also hydrophilic polyesters. Useful polyalkylene oxides have for example the formula (III)

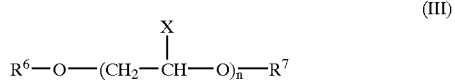

where
$R^6$ and $R^7$ are independently hydrogen, alkyl, alkenyl or aryl,
X is hydrogen or methyl, and
n is an integer from 1 to 10,000.

$R^6$ and $R^7$ are each for example linear or branched $(C_1$–$C_{10})$-alkyl, methyl, ethyl, propyl, isopropyl, n-butyl, $(C_2$–$C_6)$-alkenyl or aryl such as unsubstituted or $(C_1$–$C_4)$-alkyl-substituted phenyl.

$R^6$ and $R^7$ are each preferably hydrogen, $(C_1$–$C_4)$-alkyl, $(C_2$–$C_6)$-alkenyl or phenyl.

The hydrophilic, highly swellable hydrogels are preferably in a crdsslinked state, i.e., they containunits polymerized into the polymer network that are derived from compounds having at least two double bonds.

Usel crosslinkers include in particular methylenebisacrylamide, methylenebismethacrylamide, esters of unsaturated mono- or polycarboxylic acids with polyols, such as diacrylate or triacrylate, e.g., butanediol diacrylate, butanediol dimethacrylate, ethylene glycol diacrylate, ethylene glycol dimethacrylate and also trimethylolpropane triacrylate, allyl compounds such as allyl (meth) acrylate, triallyl cyanurate, diallyl maleate, polyallyl esters, tetraallyloxyethane, triallylamine, tetraallylethylenediamine, pentaerythritol triallyl esters or allyl esters of phosphoric acid and also vinyl compounds such as vinyl acrylate, divinyl adipate, divinylbenzene and vinylphosphonic acid derivatives, as described for example in EP-A-0 343 427.

The polymerization may be initiated using high energy electromagnetic radiation or the customary chemical polymerization initiators, for example organic peroxides such as benzoyl peroxide, tert-butyl hydroperoxide, methyl ethyl ketone peroxide, cumene hydroperoxide, azo compounds such as azodiisobutyronitrile and also inorganic peroxy compounds such as ammonium persulfate, potassium persulfate or hydrogen peroxide, with or without reducing agents such as sodium bisulfite, and iron(II) sulfate or redox systems where the reducing component is an aliphatic or aromatic sulfinic acid, such as benzenesulfinic acid or toluenesulfinic acid or derivatives thereof, for example Mannich adducts of sulfinic acid, aldehydes and amino compounds.

Polymerization in aqueous solution is preferably conducted as a gel polymerization by utilizing the Trommsdorff-Norrish effect. It is particularly preferable for the polymerization to be carried out in the quiescent state without mechanical mixing, so that the hydrogel that forms is not exposed to any mechanical shearing forces which would raise the level of extractables. The, polymerization may here be carried out not only batchwise, for example in a cylindrical reactor, but also continuously, for example by polymerization on a belt reactor.

The resultant hydrogels are coarsely comminuted by means of customary pulling and/or cutting tools, for example by the action of a discharging pump or screw in the case of a polymerization in a cylindrical reactor or by a cutting roll or cutting roll combination in the case of a belt polymerization.

The acidic hydrogel is subsequently neutralized according to the invention by destructuring and mixing the hydrogel and the neutralizing agent in a mincer comprising a system of screw, rotating blade, restricted flow zone and breaker plate and providing a power output of from 1000 to 6000 $Wh/m^3$, preferably of from 2500 to 5000 $Wh/m^3$, by passing the hydrogel through a zone having an energy dissipation density of from 400 to 800 W/1 of mixing volume. The process utilizes residence times of from 5 to 30 seconds. The frequency of the rotating blade is 1–5 $s^{-1}$, preferably 3–4 $s^{-1}$. To reduce the shearing forces on mixing in the restricted flow region above the breaker plate of the apparatus, the capillaries in the breaker plate are conical. The open area of the breaker plate is from 20 to 40%, preferably from 25 to 35%, and the initial hole diameter is from 4 to 16 mm, preferably from 8 to 10 mm, coupled with a conical widening at an angle of from 8° to 20°, preferably from 10° to 15°. A mincer is similar in equipment terms to an extruder, but exerts less shearing force.

The design described provides a combination of high mixing efficiency and of benign mechanical treatment of the mixture of hydrogel and neutralizing agent. A single-stage treatment would prove to be absolutely adequate for homogeneous distribution, avoiding the repeated mincing of the gel which would in turn lead to an undesirable increase in the shearing stress on the gel.

The choice of neutralizing agent is not critical, suitable neutralizing agents being alkali metal hydroxides, ammonia, aliphatic primary and secondary amines, alkali metal carbonates and alkali metal bicarbonates. Particular preference is given to sodium hydroxide and sodium carbonate. The neutralizing agent may be added in liquid form, for example aqueous sodium hydroxide solution, in solid form, for example sodium carbonate powder, or in gaseous form, for example ammonia.

The specific design of the mincer also makes it possible to mix other reactants or materials with the polymer gel to be neutralized according to the invention. This avoids the repeated mincing of the gel which would in turn lead to an undesirable increase in the shearing stress on the gel.

For instance, the gel may be admixed with reactants capable of reacting with free acrylic acid, for example amino acids such as cysteine or lysine, hydroxylamine and/or its salts such as hydrochloride or sulfate, hydrazine and/or its salts, ozone or sulfur compounds having a reducing effect, such as alkali metal sulfites, bisulfites or disulfiteas, sodium thiosulfate or mercapto compounds.

The gel may also be admixed with materials capable of reacting with the carboxyl groups of the hydrogel by crosslinking. Examples of such materials are polyhydric alcohols, polyacid amines, polyamidoamines and their reaction products with epichlorohydrin, di- and polyepoxides, bis- and polyaziridines, bis- and polyoxazolines, di- and polyisocyanates, ethylene carbonate or oxazolidone.

It is further possible in this stage to mix the gel with fines of superabsorbent polymers that are obtained, for example, from the production of water-swellable hydrophilic hydrogels during the grinding and subsequent classification of the dried hydrogels.

Various ways are known for drying hydrogel particles. For instance, they may be dried by the thin film drying process, for example by means of a biaxial can dryer; by the plate drying process, whereby the hydrogel polymer particles are loaded onto plates in several layers in a drying chamber in which hot air circulates; by the rotating drum process using can dryers; or by the conveyor belt process, hereinbelow also referred to as simply belt drying. Belt drying, where foraminous trays of a circle conveyor are loaded in a tunnel with the material to be dried and the material is dried by blowing hot air through the tray holes during the passage through the tunnel, constitutes the most economical drying process for water-swellable hydrophilic hydrogels and is therefore preferred. The rate of drying of the material to be dried is determined by the evaporation rate, which indicates how many kg of water evaporate per square meter of belt area per hour from the product to be dried. This evaporation rate should be as high as possible for economic reasons.

The hydrogels which have been neutralized according to the invention and which have preferably been mixed with additional reactants and/or superabsorbent fines have an economically advantagoeus drying rate for belt drying. They possess a standardized evaporation rate of at least 50 $kg/m^2h$, preferably at least 70 $kg/m^2h$, particularly preferably at least 80 $kg/m^2h$ in hot air drying at 180° C. at an air velocity of 2 m/s.

In a particularly preferred process, the standardized evaporation rate can be further enhanced by applying a release agent to the hydrogel particles beforehand. The release agents are applied without mechanical stress on the hydrogel particles by spraying in suitable equipment, for example rotary tube, Drais mixer, plowshare mixers such as Lödige mixers, Peterson-Kelly mixers, cone screw mixers, etc.

Useful release agents include nonionic, anionic, cationic or amphoteric surfactants having an HLB value of not less than 3 (for a definition of the HLB value see W. C. Griffin, J. Soc. Cosmetic Chem. 5 (1954) 249). Preference is given to surfactants which are soluble or at least dispersible in water.

Useful nonionic surfactants include for example the addition products of ethylene oxide, propylene oxide or mixtures of ethylene oxide and propylene oxide with alkylphenols, aliphatic alcohols, carboxylic acids and amines. For example $C_8$–$C_{12}$-alkylphenols which have been alkoxylated with ethylene oxide and/or propylene oxide are useful. Commercially available products of this kind include for example octylphenols or nonylphenols which have each been reacted with from 4 to 20 mol of ethylene oxide per mole of phenol. Other nonionic surfactants include ethoxylated $C_{10}$–$C_{24}$ fatty alcohols or ethoxylated $C_{10}$–$C_{24}$ fatty acids and also ethoxylated $C_{10}$–$C_{24}$ fatty amines or ethoxylated $C_{10}$–$C_{24}$ fatty amides. It is also possible to use polyhydric $C_3$–$C_6$-alcohols which have been partly esterified with $C_{10}$–$C_{24}$ fatty acids. These esters may additionally have been reacted with from 2 to 20 mol of ethylene oxide. Useful fatty alcohols for alkoxylation to prepare surfactants include for example palmityl alcohol, stearyl alcohol, myristyl alcohol, lauryl alcohol, oxo alcohols and also unsaturated alcohols, such as oleyl alcohol. The fatty alcohols are ethoxylated or propoxylated or ethoxylated and propoxylated to such an extent that the reaction products are soluble in water. Generally 1 mol of the above-indicated fatty alcohols is reacted with from 2 to 20 mol of ethylene oxide and optionally up to 5 mol of propylene oxide in such a way that surfactants having an HLB value of more than 8 are obtained.

Useful $C_3$–$C_6$-alcohols for partial esterification with or without ethoxylation include for example glycerol, sorbitol, mannitol and pentaerythritol. These polyhydric alcohols are partialy esterified with $C_{10}$–$C_{24}$ fatty acids, for example oleic acid, stearic acid or palmitic acid. The esterification with the fatty acids is carried on at most to such a degree as to leave at least one OH group of the polyhydric alcohol unesterified. Useful esterification products include for example sorbitan monooleate, sorbitan tristearate, mannitol monooleate, glycerol monooleate and glycerol dioleate. The aforementioned fatty esters of polyhydric alcohols that still contain at least one free OH group may be additionally reacted with ethylene oxide, propylene oxide or mixtures of ethylene oxide and propylene oxide for modification. Per mole of fatty ester it is preferable to use from 2 to 20 mol of the alkylene oxides mentioned. The degree of ethoxylation, as will be known, has an effect on the HLB value of nonionic surfactants. By suitably selecting the alkoxylating agent and the amount of alkoxylating agent it is possible to prepare surfactants having HLB values in the range from 3 to 20 in a technically simple manner.

A further group of useful substances are homopolymers of ethylene oxide, block copolymers of ethylene oxide and alkylene oxides, preferably propylene oxide, and also polyfunctional block copolymers formed, for example, by sequential addition of propylene oxide and ethylene oxide onto diamines.

It is further possible to use alkylpolyglycosides as marketed for example by Henkel under the trade marks APG®, Glucopan® and Plantaren®.

Nonionic surfactants can be used either alone or else mixed with each or one another.

Useful anionic surfactants include $C_8$–$C_{24}$-alkylsulfonates, which are preferably used in the form of the alkali metal salts, $C_8$–$C_{24}$-alkyl sulfates, which are preferably used in the form of the alkali metal or trialkanolammonium salts, e.g., triethanolammonium laurylsulfate, sulfosuccinic diesters, for example the sodium salt of di(2-ethylhexyl)sulfosuccinate, sulfosuccinic monoesters, for example sodium lauryl sulfosuccinate or disodium fatty alcohol polyglycol ether sulfosuccinate, $C_8$–$C_{24}$-alkylarylsulfonic acids and also the sulfuric monoesters of addition products of ethylene oxide with alkylphenols or fatty alcohols.

Examples of useful cationic surfactants are the salts of fatty amines, for example cocoammonium acetate, quaternary fatty acid amino esters, for example difatty acid isopropyl ester dimethylammonium methosulfate, quaternary fatty acid aminoamides, for example N-undecylenic propylamido N-trimethylammonium methosulfate, addition products of alkylene oxides with fatty amines or salts of fatty amines, for example pentaethoxystearylammonium acetate or ethoxylated methyloleinamine methosulfate and also long-chain alkylbenzyldimethylammonium compounds, such as $C_{10}$–$C_{22}$-alkylbenzyldimethylammonium chloride.

Examples of useful amphoteric surfactants are compounds bearing in one and the same molecule at least one quaternary ammonium cation and at least one carboxylate or sulfate anion, for example dimethylcarboxymethyl fatty acid alkylamidoammonium betaines or 3-(3-fatty acid amidopropyl)dimethylammonium 2-hydroxypropanesulfonates.

Ionic surfactants can be used alone or else mixed with each or one another.

Surfactants are used in amounts of from 0.001 to 5%, preferably from 0.01 to 2%, by weight based on the solids content of the polymer gel to be dried. Preference is given to the use of nonionic or anionic surfactants, and particular preference to the use of nonionic surfactants, such as the products of reacting 2–20 mol of ethylene oxide with the partial ($C_{10}$–$C_{24}$) fatty acid esters of polyhydric ($C_3$–$C_6$)-alcohols or the aforementioned esterification products which have not been reacted with ethylene oxide.

Useful release agents further include silicones such as polysiloxanes containing one or more selected from the group consisting of methyl, ethyl, propyl and phenyl as organic radicals. Preference is given to polydimethylsiloxanes and polymethylphenylsiloxanes and particular preference is given to polydimethylsiloxanes. Polysiloxanes may be chain or cyclical polymers, preference being given to those having a linear construction, especially polydimethylsiloxanes having a linear construction. It is further preferable to use silicones or polysiloxanes in the form of the commercially available products, which customarily constitute a mixture of substances and may also be modified silicones, for example aminosiloxanes. Preferred commercially available liquid silicones are the products generally referred to as silicone oils, and particular preference is given in turn to silicon oils based on dimethylpolysiloxane, specifically on polydimethylsiloxane having a linear construction. Preference is finally given to siloxanes having a 25° C. viscosity of from 5 to 20,000 cSt, particularly preferably from 50 to 350 cSt, most preferably from 80 to 120 cSt, specifically those having a 25° C. viscosity of about 100 cSt.

Examples of other, similarly useful release agentsare hexadecanol, octadecanol, hexadecyl acetate, octadecyl acetate, $C_{12}$–$C_{24}$-fatty acids and salts thereof, e.g., palmitic acid and its salts or stearic acid and its salts, methyl palmitate, butyl stearate, butyl oleate, hexylene glycol, octamethylene glycol, octadecane, eicosane, commercially available paraffin oils and paraffins wherein for example paraffinic, naphthenic and aromatic hydrocarbons may be included, having a melting point of not more than 100° C. and a vapor pressure of not more than 0.1 mbar at 20° C.

A further group of useful-lrelease agents are polyglycols and polyglycol derivatives, especially polyalkylene glycols and polyalkylene glycol ethers, especially the mono- and dialkyl ethers. Particular preference is given to polyethylene glycols, polypropylene glycols, ethylene oxide-propylene oxide interpolymers, especially block polymers, mono- and di($C_1$–$C_4$)alkyl, especially methyl, ethers of polyethylene glycol and polypropylene glycol, but also polyglycol ethers of higher molecular weight fatty alcohols. It is again preferable to use polyglycols and polyglycol ethers in the form of commercially available products, which customarily constitute a mixture of different substances, especially substances having different molecular weights.

In a preferred embodiment of the process, the release agent used is a neutralizing agent. Any neutralizing agent may be used which is also suitable for neutralizing the acidic hydrogel in the mincer. The neutralization in the mincer is preferably carried on to a degree of neutralization of not less than 50% by weight, preferably not less than 55% by weight, particularly preferably not less than 60% by weight. By additional treatment, for example by spraying hydrogel particles with the neutralizing agent or its aqueous solution, i.e., without mechanical shearing stress on the gel particles, the degree of neutralization is raised to the desired ultimate degree of neutralization. The neutralizing agent in the second step may be identical to or different from the neutralizing agent in the first step. The second neutralizing step is preferably carried out using aqueous sodium hydroxide solution.

The hydrogels which have thus been neutralized according to the invention and which have optionally been mixed with additional reactants and/or superabsorbent fines and which have subsequently been sprayed with a release agent in the manner described have an economically very advantageous drying rate for belt drying. In hot air drying at 180° C. and an air velocity of 2 m/s they provide a standardized evaporation rate of not less than 90 kg/m²h, preferably not less than 120 kg/m²h, particularly preferably not less than 140 kg/m²h.

The hydrogel particles are subsequently dried. Belt drying is particularly preferable from an economic viewpoint. As well as factors to be optimized, such as the distribution of the hydrogel particles on the belt, the bed height of the hydrogel particles, the drying temperature or drying temperature profile, the relative humidity of the dryer air, air velocity, air distribution and air direction, it is the structure of the hydrogel particle bed which has a decisive influence on the rate of drying. The highest rates of drying are provided by loose, fluffy, separated gel particles, as provided by the process of the invention.

For the subsequent grinding of the dried hydrogel particles it is advantageous to cool the dried material to temperatures <70° C., preferably <60° C., particularly preferably <50° C., in the last section of the belt drying stage. The dried, cooled hydrogel particles are initially prebroken, for example by means of a knuckle-type crusher (precomminutor). The thus precomminuted hydrogel particles are then ground, preferably by means of one or more successive roll mills in order that the production of fines may be minimized. In a particularly preferred embodiment, the grinding is carried out twice, first via a coarse roll mill and then via a fine roll mill, and the latter may in turn be carried out in one or two stages. Sieving is carried out subsequently to set the particle size distribution, which is generally in the range from 100 to 1000 μm, preferably from 120 to 850 μm. Oversize particles may be resubmitted to grinding, while undersize particles may be recycled back into the production process, for example by mixing with the gel to be neutralized in the postneutralization step in the mincer, or be used for distinct purposes.

In a preerred embodiment of the invention, the absorption properties of the hydrophilic, highly swellable hydrogels thus obtained are still further improved by a subsequent, preferably covalent, surface postcrosslinking step. In this step, compounds capable of reacting with the carboxyl groups of the hydrogel by crosslinking are applied to the surface of the hydrogel particles, preferably in the form of an aqueous solution. Useful postcrosslinking agents include for example di- or polyglycidyl compounds such as phosphonyl diglycidyl ether or ethylene glycol diglycidyl ether, alkoxysilyl compounds, polyaziridines, polyamines or polyamidoamines and also their rection products with epichlorohydrin, polyols such as ethylene glycol, 1,2-propanediol, 1,4-butanediol, glycerol, di- and polyglycerol, pentaerythritol, sorbitol, the ethoxylates of these polyols and their esters with carboxylic acids or carbonic acid, ethylene carbonate, propylene carbonate, oxazolidone, bisoxazoline, polyoxazolines, di- and polyisocyanates. If necessary, acidic catalysts such as, for example, p-toluenesulfonic acid, phosphoric acid, boric acid or ammonium dihydrogenphosphate can be added.

Suitable mixing assemblies for spraying the hydrogel particles with crosslinker solution include for example Patterson-Kelly mixers, DRAIS turbulence mixers, Lödige mixers, screw mixers, plate mixers, fluidized bed mixers, Schugi mixers. The spraying of the crosslinker solution may be followed by a temperature treatment step, preferably in a downstream dryer, at from 80 to 230° C., preferably 80–190° C., particularly preferably from 100 to 160° C., for from 5 minutes to 6 hours, preferably from 10 minutes to 2 hours, particularly preferably form 10 minutes to 1 hour; lysis products may be removed as well as solvent fractions.

In a particularly preferred embodiment of the invention the hydrophilicity of the hydrogel particle surface is additionally modified through formation of metal complexes. The formation of metal complexes on the outer shell of the hydrogel particles is effected by spraying with solutions of divalent or more highly valent metal salt solutions to allow the metal cations to react with the carboxyl groups of hydrogel to form complexes. Examples of di- or more highly valent metal cations are $Mg^{2+}$, $Ca^{2+}$, $Al^{3+}$, $Sc^{3+}$, $Ti^{4+}$, $Mn^{2+}$, $Fe^{2+}/Fe^{3+}$, $Co^{2+}$, $Ni^{2+}$, $Cu^+/Cu^{2+}$, $Zn^{2+}$, $Y^{3+}$, $Zr^{4+}$, $Ag^+$, $La^{3+}$, $Ce^{4+}$, $Hf^{4+}$, and $Au^+/Au^{3+}$, preferred metal cations being $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $zr^4+$. Metal cations may be used alone or else as a mixture with each or one another. Of the metal cations mentioned, any metal salt possessing sufficient solubility in the solvent to be used is suitable. Metal salts with weakly complexing anions, for example, chloride, nitrate or sulfate, are particularly suitable. Useful solvents for the metal salts include water, alcohols, DMF, DMSO and mixtures thereof. Particular preference is given to water and water/alcohol mixtures, for example water/methanol or water/1,2-propanediol.

The spraying of the metal salt solution onto the hydrogel particles may take place both before and after the surface postcrosslinking of hydrogel particles. In a particularly preferred process, the spraying on of the metal salt solution takes place in the same step as the spraying on of the crosslinker solution, the two solutions being sprayed on separately in succession or simultaneously via two nozzles, or crosslinker solution and metal salt solution may be sprayed on together via a single nozzle.

Optionally, the hydrogel particles may be further modified by admixture of finely divided inorganic solids, for example silica, alumina, titania and iron(II) oxide to further augment the effects of the surface aftertreatment. Particular preference is given to the admixture of hydrophilic silica or of alumina having an average primary particle size of from 4 to 50 nm and a specific surface area of 50–450 m$^2$/g. The admixture of finely divided inorganic solids preferably takes place after the surface modification through crosslinking/complexing, but may also be carried out before or during these surface modifications.

Hydrogels of the invention are notable for outstanding absorbency coupled with high gel strength and low levels of extractabies and are therefore very useful as absorbants for water and aqueous fluids, especially body fluids, for example urine or blood, for example in hygiene articles such as, for example, infant and adult diapers, sanitary napkins, tampons and the like. But they may also be used as soil improvers in agriculture and market gardening, as moisture binders in cable sheathing and also for thickening aqueous wastes.

Description of test methods used in examples:

CRC (Centrifuge Retention Capacity):

0.2 g of hydrogel (particle size fraction 106–850 μm) is weighed into a teabag 60×60 mm in size, which is subsequently welded shut. The teabag is then placed in an excess of 0.9% by weight sodium chloride solution (at least 1.25 l of sodium chloride solution/1 g of hydrogel). After a swelling time of 20 minutes, the teabag is removed from the sodium chloride solution and centrifuged at 250 g for three minutes. The centrifuged teabag is weighed to determine the amount of liquid retained by the hydrogel.

Extractables (16 h):

1 g of hydrogel (particle size fraction 106–850 μm) is stirred into 200 ml of 0.9% by weight sodium chloride solution. The beaker is sealed and the mixture is stirred for 16 h. This is followed by filtration through a 0.22 μm filter and determination of the level of extractables by an acid-base titration of the carboxyl groups (titration with 0.1 normal NaOH to pH 10, then with 0.1 normal HCl to pH 2.7).

AUL (Absorbency under Load):

Absorbency under Load (AUL) was determined in known manner as described for example in EP-A-0 339 461. AUL 70 indicates a measurement of the absorbency under a load of 70 g/cm$^2$, the area coverage of the hydrogel particles (partice size fraction 106–850 μm) in the measuring cell being 0.032 g/cm$^2$.

Gel Column Test:

The apparatus is a glass column 2.6 cm in diameter and not less than 40 cm in length which has a 0 porosity frit and a tap at the lower end. The glass column drains into a beaker standing on a balance. Its weight is recorded continuously, for example by means of a computer. To carry out the gel column test, 1 g of hydrogel is allowed to swell in 100 g of 0.9% by weight NaCl solution for 5 minutes. The swollen gel is transferred into the glass column. To condition the gel, 100 ml of 0.9% by weight NaCl solution are added, the tap is opened and the emergence of liquid having passed through the swollen gel layer is awaited. The tap is then closed and another 100 g of 0.9% by weight NaCl solution are added. After opening of the tap, the amount of liquid passing through is recorded as a function of time. The amount of liquid which has passed through after 60 seconds is the 60 s flowthrough value.

Gel Strength:

Gel strength is measured using a Carri-Med-Stress rheometer having a plate-plate configuration. 1 g of hydrogel is allowed to swell in 60 g of 0.9% by weight sodium chloride solution for 24 hours and subsequently the storage modulus G' of this swollen gel is measured as a function of the shear stress at a frequency of 1 Hz. The plateau value is reported as the gel strength.

Determination of Standardized Evaporation Rate:

The standardized evaporation rate is determined using a convection belt dryer simulator under the following standardized conditions:

| | |
|---|---|
| Standardized initial moisture content of hydrogel: | 30% |
| Standardized final moisture content of hydrogel: | 5% |
| Bed height of hydrogel: | 40 mm |
| Air velocity: | 2.0 m/s. |

EXAMPLES

Polymerization

Inventive Example 1

In a makeup vessel 1, a mixture of 367.7 kg of demineralized water, 130.0 kg of acrylic acid, 1.0 kg of pentaerythritol triallyl ether, 220 g of 2,2'-azobisamidinopropane dihydrochloride and 400 g of potassium peroxodisulfate was deoxygenated and conditioned to 4° C. A further makeup vessel 2 was used to prepare a deoxygenated solution of 40 g of ascorbic acid in 20 kg of water. After the solutions had been prepared, the contents of the two makeup vessels were synchronously injected into a polymerization reactor under a pressure of 1.5 bar in countercurrent with nitrogen, the two solutions being mixed by a static mixer before entry into the reactor. The polymerization reactor is a 600 l tube 0.50 m in diameter with a conical taper at the end. The tubular reactor was then sealed and the reaction solution was left to stand without stirring. The ensuing polymerization, in the course of which the temperature rises to about 86° C., produces a solid gel. After cooling to room temperature overnight, a nitrogen pressure of 6 bar was injected at the top of the reactor. After the check valve situated at the end of the cone of the reactor was opened, the gel was dischargeable by means of a pump. In the course of the pumping, the gel was comminuted and was directly usable in that form for further gel workup.

Inventive Example 2

An aluminized tetrafluoroethylene-ethylene copolymer film was secured to the surface of an endless belt made of stainless steel and having a width of 450 mm and an effective length of 3000 mm in such a way that the metallized surface was in contact with the belt surface. The endless belt was introduced into a nitrogen-filled chamber to maintain the oxygen concentration at not more than 1% by volume, while spray means were disposed in such a way that hot or cold water was sprayable onto the back of the endless belt. The endless belt moved at a speed of 100 mm/min and 15° C. water was sprayed onto the belt from below.

A makeup vessel 1 was charged with 5080 parts by weight of demineralized water, 669 parts by weight of sodium bicarbonate were suspended therein, and a mixture of 2294 parts by weight of acrylic acid and 8 parts by weight of allyl methacryate was gradually metered in at a rate such that overfoaming of the reaction solution was avoided, the reaction solution cooling down to about 3–5° C. At 4° C., 2.2 parts by weight of 2,2'-azobisamidinopropane dihydrochloride (dissolved in 20 parts by weight of demineralized water) and 4 parts by weight of potassium peroxodisulfate (dissolved in 150 parts by weight of demineralized water) were added in succession and thoroughly stirred in. A second makeup vessel 2 was used to prepare a solution of 0.4 part by weight of ascorbic acid in 50 parts by weight of demineralized water.

The solutions from makeup vessels 1 and 2 were then applied continuously at a rate of 135 l/h to one end of the moving belt via a static mixer in a ratio of 80:1.

Under the abovementioned conditions, the time within which the monomer solution is subjected to polymerization on the moving belt is 30 minutes and the thickness of the monomer solution layer on the belt was about 5 cm.

At the other end of the endless belt, a polymer gel was obtained in the form of a strand about 5 cm in thickness 30 minutes from the start of the aqueous monomer solution feed. This polymer gel strand was detached from the belt surface and directly introduced into a cutting means of the roll type. This provided comminuted hydrogel particles which were directly suitable for further gel workup.
Gel Workup:

Inventive Example 3

The hydrogel obtained in Inventive Example 1 was neutralized using a mincer as per claim 1, the power output being 4000 Wh/m$^3$, the frequency of the rotating blade 3 s$^{-1}$, the energy dissipation density 600 W/l of mixing volume, the residence time of the hydrogel in the mincer 20 s, the open area of the breaker plate 32% and the hole initial diameter of the open areas 10 mm coupled with a conical widening at an angle of 12°. The hydrogel is introduced into the above-described mincer together with a 50% by weight solution of sodium hydroxide, the quantitative proportions of hydrogel and sodium hydroxide solution being chosen so as to produce a 74 mol % average degree of neutralization for the acrylic acid units of the.hydrogel. The pH homogeneity of the singly minced hydrogel was verified by spraying with a pH indicator solution. The minced hydrogel was then hot air dried at an air temperature of 180° C. and an air velocity of 2 m/s to determine the standardized evaporation rate. The dried hydrogel was tested for extractables.

| pH homogeneity of gel | Standardized evaporation rate | Extractables |
|---|---|---|
| homogeneous | 75 kg/m$^2$h | 3.5% |

Comparative Example 1

Inventive Example 1 was repeated except that the mincing or, chopping was carried out in a commercially available meat grinder having the following characteristics:

| Power: | 3500 Wh/m$^3$ |
| Frequency of rotating blade: | 4 s$^{-1}$ |

| Energy dissipation density: | 100 W/l of mixing volume |
| Hydrogel residence time: | 4 s |
| Open area of breaker plate: | 35% |
| Hole initial diameter of open areas: | 10 mm (no conical widening) |

| pH homogeneity of gel | Standardized evaporation rate | Extractables |
|---|---|---|
| Inhomogeneous, about 30% of gel too acidic (pH < 4.5) and about 30% too alkaline (pH > 8.5) | 35 kg/m$^2$h | 4.0% |

Single use of a mincer or grinder not according to the invention thus does not provide homogeneous neutralization of the acrylic acid units of the hydrogel. The chopped hydrogel had a substantially lower standardized evaporation rate.

Comparative Example 2

Comparative Example 1 was repeated except that chopping was carried out three times to obtain homogeneous neutralization.

| pH homogeneity of gel | Standardized evaporation rate | Extractables |
|---|---|---|
| homogeneous | 40 kg/m$^2$h | 10.5% |

Repeated chopping did provide homogeneous neutralization, but only at the cost of a substantial rise in extractables. The chopped hydrogel had a substantially lower standardized evaporation rate than in Inventive Example 3.

Inventive Example 4

The hydrogel obtained in Inventive Example 2, 0.7% by weight (based on acrylic acid) of solid substance of a commercially available caticnic polyamidoamine resin (KYMENE 557H® from Hercules Corp., USA), 20% by weight (based on acrylic acid) of superabsorbent fines (90% of particles smaller than 120 μm) and a 50% by weight solution of sodium hydroxide were introduced into a mincer having the following characteristics:

| Power: | 5000 Wh/m$^3$ |
| Frequency of rotating blade: | 3 s$^{-1}$ |
| Energy dissipation density: | 750 W/l of mixing volume |
| Hydrogel residence time: | 25 s |
| Open area of breaker plate: | 30% |
| Hole initial diameter of open areas: | 8 mm (with conical widening at an angle of 15°), | the quantitative proportions of hydrogel and sodium hydroxide solution being chosen so as to provide a 70 mol % average degree of neutralization for the acrylic acid units of the hydrogel. The pH homogeneity of the singly minced hydrogel was verified by spraying with pH indicator solution. The minced hydrogel was then hot air dried at an air temperature of 180° C. and an air velocity of 2 m/s to determine the standardized evaporation rate. The dried hydrogel was tested for extractables.

| pH homogeneity of gel | Standardized evaporation rate | Extractables |
|---|---|---|
| homogeneous | 79 kg/m²h | 1.5% |

Single mincing provided homogeneous neutralization even on addition of superabsorbent fines and of an additional reactant.

Inventive Example 5

The hydrogel obtained in Inventive Example 1 was introduced into the mincer described in Inventive Example y together with a 50% by weight solution of sodium hydroxide, the quantitative proportions of hydrogel and sodium hydroxide solution being chosen so as to provide a 74 mol % average degree of neutralization for the acrylic acid units of the hydrogel. The hydrogel particles were subsequently sprayed with various release agents as per the table which follows in a continuous Drais mixer. Very loose, fluffy gels with distinct gel particles were obtained. The hydrogels were then hot air dried at an air temperature of 180° C. and an air velocity of 2 m/s to determine the standardized evaporation rate.

| Release agent | % by weight of release agent based on acrylic acid | Standardized evaporation rate |
|---|---|---|
| Sorbitan monococoate | 0.2% | 110 kg/m²h |
| Hostapur ® SAS 30 | 0.3% | 125 kg/m²h |
| C₁₂—C₁₄-Alkylbenzyl-dimethylammonium chloride | 0.25% | 95 kg/m²h |
| Ampholyt ® JB 130/K | 0.20% | 105 kg/m²h |
| PEG 300 | 0.35% | 115 kg/m²h |
| MPG 350 | 0.35% | 130 kg/m²h |
| PIONIER ® 2024 | 0.1% | 120 kg/m²h |
| BAYSILONE ® M 100 | 0.1% | 150 kg/m²h |
| GENAPOL ® PF 40 | 0.15% | 115 kg/m²h |
| Palmitic acid, sodium salt | 0.2% | 100 kg/m²h |
| Butyl oleate | 0.05% | 140 kg/m²h |

Hostapur ® SAS 30 (commercial product from Clariant GmbH) is a mixture of n-alkanesulfonates prepared by sulfoxidation of n-paraffins
Ampholyt ® JB 130/K (commercial product from Huls AG) is a cocoamidopropylbetaine
PEG 300 is polyethylene glycol having an average molecular weight of 300 g/mol
MPG 350 is methylpolyethylene glycol having an average molecular weight of 350 g/mol
PIONIER ® 2024 (commercial product from Hansen & Rosenthal) is a technical grade paraffin oil
BAYSILONE ® M 100 (commercial product from Bayer AG) is a polydimethylsiloxane
GENAPOL ® PF 40 (commercial product from Clariant GmbH) is an ethylene oxide-propylene oxide block copolymer.

The comparison with Inventive Example 3 showed that the treatment of the gel particles subsequent to mincing provided an increase in the standardized evaporation rate.

Inventive Example 6

The hydrogel obtained in Inventive Example 2 was introduced into the mincer described in Inventive Example 4 together with pulverulent sodium carbonate, the quantitative proportions of hydrogel and sodium carbonate being chosen so as to provide a 60 mol % average degree of neutralization for the acrylic acid units of the hydrogel. The hydrogel particles were subsequently sprayed with various neutralizing agents as per the table in a continuous rotary tube mixer so as to produce a 70 mol % final degree of neutralization for the acrylic acid units of the hydrogel. This provided very loose, fluffy gels having distinct gel particles. The hydrogels were then hot air dried at an air temperature of 180° C. and an air velocity of 2 m/s to determine the standardized evaporation rate.

| Neutralizing agent | Standardized evaporation rate |
|---|---|
| 50% by weight of aqueous sodium hydroxide solution | 125 kg/m²h |
| 50% by weight of aqueous potassium hydroxide solution | 140 kg/m²h |
| Sodium carbonate (15% by weight aqueous solution) | 115 kg/m²h |
| Potassium carbonate (40% by weight aqueous solution) | 130 kg/m²h |
| Ammonia (25% by weight aqueous solution) | 95 kg/m²h |

The comparison with Inventive Example 4 showed that the treatment of the gel particles subsequent to mincing provided an increase in the standardized evaporation rate.

Surface Postcrosslinking:

Inventive Example 7

A 100 l capacity Lödige plowshare mixer is charged with 35 kg of hydrogel powder prepared as per Inventive Example 3. A solution of 28 g of ethylene glycol diglycidyl ether, 1170 g of water and 580 g of 1,2-propanediol was injected over 5–10 minutes. The product temperature was raised to 120° C. and maintained for 60 minutes at that level to distill the solvent back off. The batch is subsequently cooled and the product discharged and classified to a particle size fraction of 120–850 µm. The product obtained was characterized by the following physical data, all measured in 0.9% by weight sodium chloride solution:

| | |
|---|---|
| CRC = | 33 g/g |
| AUL 70 = | 25 g/g |
| Gel strength = | 2500 Pa |
| Extractables 16 h= | 1.6% |
| Gel column, 60 s flowthrough value = | 90 g |

Inventive Example 8

A 10 l capacity Patterson & Kelly mixer was charged with 6 kg of hydrogel powder prepared as per Inventive Example 4. A solution of 12 g of bisoxazoline, 9 g of aluminum sulfate, 225 g of isopropyl alcohol and 225 g of water was injected into the agitated initial charge over 5 minutes and mixed in for 1 minute. The product was subsequently conditioned in a drying cabinet at 185° C. for 30 minutes. It was characterized by the following physical data, all measured in 0.9% by weight sodium chloride solution:

| | |
|---|---|
| CRC = | 27 g/g |
| AUL 70 = | 26 g/g |
| Gel strength = | 4000 Pa |
| Extractables 16 h = | 0.4% |
| Gel column, 60 s flowthrough rate = | 98 g |

Inventive Example 9

A 100 l capacity Lödige plowshare mixer was charged with 35 kg of hydrogel powder prepared as per Inventive Example 5 using Hostapur® SAS 30 as a release agent. A solution of 105 g of KYMENE 557H®, 1400 g of water and 1400 g of methanol was injected over 5–10 minutes. The product temperature was raised to 150° C. and maintained at that level for 45 minutes to distill the solvent back off. The batch is subsequently cooled, the product discharged, mixed with 0.2% by weight of hydrophilic silica (Aerosil 200) and classified to a particle size fraction of 120–850 μm. The product obtained is characterized by the following physical data, all measured in 0.9% by weight sodium chloride solution:

| | |
|---|---|
| CRC = | 31 g/g |
| AUL 70 = | 26 g/g |
| Gel strength = | 3000 Pa |
| Extractables 16 h = | 1.2% |
| Gel column, 60 s flowthrough value = | 96 g |

Inventive Example 10

A 10 l capacity Patterson & Kelly mixer was charged with 6 kg of hydrogel powder prepared as per Inventive Example 6 using aqueous sodium hydroxide solution as second neutralizing agent. A solution of 12 g of oxazblidone, 800 g of ethanol and 270 g of water was injected into the agitated initial charge over 5 minutes and mixed in for 2 minutes. The product was subsequently conditioned in a drying cabinet at 195° C. for 30 minutes. It was characterized by the following physical data, all measured in 0.9% by weight sodium chloride solution:

| | |
|---|---|
| CRC = | 28 g/g |
| AUL 70 = | 26 g/g |
| Gel strength = | 4200 Pa |
| Extractables 16 h = | 0.5% |
| Gel column, 60 s flowthrough value | 99 g |

The surface-postcrosslinked hydrogels obtained according to Inventive Examples 7 to 10 are notable for outstanding absorbency coupled with high gel strength, high gel permeability and low extractables contents and are therefore very useful as absorbants for water and aqueous fluids, especially body fluids, for example urine or blood, for example in hygiene articles such as, for example, infant and adult diapers, sanitary napkins, tampons and the like.

We claim:

1. A process for preparing a water-swellable hydrophilic polymer, comprising:

neutralizing an acidic hydrogel having a degree of neutralization of 0–40 mol % by mixing with a neutralizing agent in a mincer which comprises at least one screw, a rotating blade, a restricted flow zone and a breaker plate, to obtain neutralized and minced hydrogel particles having a final degree of neutralization of 60–85 mol %;

wherein said mincer has a power output of from 1000 to 6000 Wh/m$^3$;

wherein the acidic hydrogel passes through a zone having an energy dissipation density of from 400 to 800 W/1 of mixing volume;

wherein an average residence time of the hydrogel in the mincer is from 5 to 30 seconds; and wherein the breaker plate has an open area of from 20 to 40%.

2. The process of claim 1, further comprising adding, during said neutralizing in the course of mincing, one or more other reactive materials capable of reacting with at least one component selected from the group consisting of acrylic acid, a carboxyl group of the acidic hydrogel, a water-swellable hydrophilic polymer fine or a mixture thereof.

3. The process of claim 1, wherein the neutralized, minced hydrogel particles are sprayed with a release agent without mechanical shearing stress before placing on the belt dryer.

4. The process of claim 1, wherein said neutralizing is carried out in two steps;

wherein a first step takes place in the mincer; and wherein a second step is effected by applying the neutralizing agent to the hydrogel particles without mechanical shearing stress.

5. The process of claim 1, wherein the grinding of the dried, neutralized hydrogel particles is effected in one or more successive roll mills.

6. The process of claim 1, further comprising:

a) free-radically polymerizing or copolymerizing one or more hydrophilic acid-functional monomers without mixing to obtain an acidic hydrogel; or graft polymerizing or copolymerizing one or more hydrophilic acid-functional monomers onto a grafting base without mixing to obtain an acidic hydrogel;

wherein an average degree of neutralization of the acid-functional monomers is from 0 to 40 mol %;

b) coarsely comminuting said acidic hydrogel;

c) neutralizing said acidic hydrogel by mixing with a neutralizing agent in a mincer which comprises at least one screw, a rotating blade, a restricted flow zone and a breaker plate, to obtain neutralized, minced hydrogel particles having a final degree of neutralization of 60–85 mol %;

wherein the mincer has a power output of from 1000 to 6000 Wh/m$^3$;

wherein the hydrogel passes through a zone having an energy dissipation density of from 400 to 800 W per 1 of mixing volume;

wherein an average residence time of the acidic hydrogel in the mincer is from 5 to 30 seconds; and wherein the breaker plate has an open area of from 20 to 40%;

d) placing the neutralized, minced hydrogel particles without further mechanical shearing stress onto a belt dryer;

e) drying the neutralized, minced hydrogel particles using said belt dryer, to obtain dried, neutralized hydrogel particles; and f) grinding and sieving the dried, neutralized hydrogel particles to obtain ground, dried, neutralized hydrogel particles.

7. The process of claim 6, wherein said hydrophilic acid-functional monomer is a compound of formula (I)

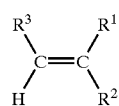

wherein $R^1$ is hydrogen, methyl or ethyl;

$R^2$ is —COOR$^4$, hydroxysulfonyl, phosphonyl, a ($C_1$–$C_4$)-alkanol-esterified phosphonyl group aria group of formula (II)

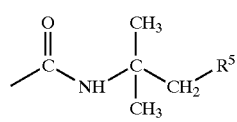

$R^3$ is hydrogen, methyl, ethyl or carboxyl;

$R^4$ is hydrogen, amino-($C_1$–$C_4$)-alkyl or hydroxy-($C_1$–$C_4$)-alkyl; and $R^5$ is hydroxysulfonyl, phosphonyl or carboxyl.

8. The process of claim 6, wherein said grafting base is selected from the group consisting of starch, cellulose, cellulose derivatives, polyvinyl alcohol, polyalkylene oxide, polyethylene oxide, polypropylene oxide and hydrophilic polyesters.

9. The process of claim 6, wherein the polymerizing or copolymerizing of the hydrophilic acid-functional monomer is effected in the presence of a crosslinker.

10. The process of claim 6, wherein the neutralized, minced hydrogel particles have a standardized evaporation rate of at least 50 kg/m$^2$h on hot air drying at 180° C. and in an air velocity of 2 m/s.

11. The process of claim 6, further comprising covalently surface postcrosslinking said ground, dried, neutralized hydrogel particles.

12. The process of claim 6, further comprising modifying a surface of the ground, dried, neuralized hydrogel particles by forming of a metal complex.

13. A method of adsorbing water and aqueous fluids, comprising:

contacting a water-swellable hydrophilic polymer obtained by the process of claim 1 with water, an aqueous fluid or both.

14. The method of claim 13, wherein said aqueous fluid is a fluid from the human body.

15. A process for preparing a water-swellable hydrophilic polymer, comprising:

a) free-radically polymerizing or copolymerizing one or more hydrophilic acid-functional monomers to obtain an acidic hydrogel; or graft polymerizing or copolymerizing one or more hydrophilic acid-functional monomers onto a grafting base to obtain an acidic hydrogel;

wherein an average degree of neutralization of the acid-functional monomers is from 0 to 40 mol %;

b) coarsely comminuting said acidic hydrogel;

c) neutralizing said acidic hydrogel by mixing with a neutralizing agent in a mincer which comprises at least one screw, a rotating blade, a restricted flow zone and a breaker plate, to obtain neutralized, minced hydrogel particles having a final degree of neutralization of 60–85 mol %;

wherein the mincer has a power output of from 1000 to 6000 Wh/m$^3$;

wherein the hydrogel passes through a zone having an energy dissipation density of from 400 to 800 W per 1 of mixing volume;

wherein an average residence time of the acidic hydrogel in the mincer is from 5 to 30 seconds; and wherein the breaker plate has an open area of from 20 to 40%;

d) placing the neutralized, minced hydrogel particles without further mechanical shearing stress onto a belt dryer;

e) drying the neutralized, minced hydrogel particles using said belt dryer, to obtain dried, neutralized hydrogel particles; and f) grinding and sieving the dried, neutralized hydrogel particles to obtain ground, dried, neutralized hydrogel particles.

16. The process of claim 15, wherein said polymerizing is effected without mixing.

17. The process of claim 15, wherein said hydrophilic acid-functional monomer is a compound of formula (I)

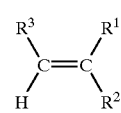

wherein $R^1$ is hydrogen, methyl or ethyl;

$R^2$ is —COOR$^4$, hydroxysulfonyl, phosphonyl, a ($C_1$–$C_4$)-alkanol-estenfied phosphonyl group or a group of the formula (II)

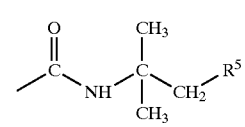

$R^3$ is hydrogen, methyl, ethyl or carboxyl;

$R^4$ is hydrogen, amino-($C_1$–$C_4$)-alkyl or hydroxy-($C_1$–$C_4$)-alkyl; and $R^5$ is hydroxysulfonyl, phosphonyl or carboxyl.

18. The process of claim 15, wherein said grafting base is selected from the group consisting of starch, cellulose, cellulose derivatives, polyvinyl alcohol, polyalkylene oxide, polyethylene oxide, polypropylene oxide and hydrophilic polyesters.

19. The process of claim 15, wherein the polymerizing or copolymerizing of the hydrophilic acid-functional monomer is effected in the presence of a crosslinker.

20. The process of claim 15, wherein the neutralized and minced hydrogel particles have a standardized evaporation rate of at least 50 kg/m$^2$h on hot air drying at 180° C. and in an air velocity of 2 m/s.

21. The process of claim 15, further comprising adding, during said neutralizing in the course of mincing, one or more other reactive materials capable of reacting with at least one component selected from the group consisting of acrylic acid, a carboxyl group of the acidic hydrogel a water-swellable hydrophilic polymer fine or a mixture thereof.

22. The process of claim 15, wherein the neutralized, minced hydrogel particles are sprayed with a release agent without mechanical shearing stress before placing on the belt dryer.

23. The process of claim 15, wherein said neutralizing is carried out in two steps;
   wherein a first step takes place in the mincer; and
   wherein a second step is effected by applying the neutralizing agent to the hydrogel particles without mechanical shearing stress.

24. The process of claim 15, wherein the grinding of the dried, neutralized hydrogel particles is effected in one or more successive roll mills.

25. The process of claim 15, further comprising covalently surface postcrosslinking said grinded, dried, neutralized hydrogel particles.

26. The process of claim 15, further comprising modifying a surface of the dried and ground, dried, neutralized hydrogel particles by forming of a metal complex.

* * * * *